United States Patent [19]

Dixon

[11] Patent Number: 5,514,868
[45] Date of Patent: May 7, 1996

[54] REDUCING INTERFERENCES, IN PLASMA SOURCE MASS SPECTROMETERS

[75] Inventor: Andrew Dixon, Uttoxeter, United Kingdom

[73] Assignee: Fisons Plc, Ipswich, England

[21] Appl. No.: 403,842

[22] PCT Filed: Sep. 15, 1993

[86] PCT No.: PCT/GB93/01949

§ 371 Date: Mar. 14, 1995

§ 102(e) Date: Mar. 14, 1995

[87] PCT Pub. No.: WO94/07257

PCT Pub. Date: Mar. 31, 1994

[30] Foreign Application Priority Data

Sep. 15, 1992 [GB] United Kingdom .............. 9219457

[51] Int. Cl.[6] .............. H01J 49/26; H01J 49/44; B01D 59/44
[52] U.S. Cl. .............. 250/282; 250/288; 250/305
[58] Field of Search .............. 250/281, 282, 250/288, 305

[56] References Cited

U.S. PATENT DOCUMENTS

| | | | |
|---|---|---|---|
| 3,859,226 | 1/1975 | Schillalies | 250/282 |
| 4,746,794 | 5/1988 | French et al. | 250/288 |
| 4,769,542 | 9/1988 | Rockett | 250/305 |
| 5,068,534 | 11/1991 | Bradshaw et al. | 250/288 |
| 5,352,893 | 10/1994 | Freedman | 250/281 |
| 5,420,423 | 5/1995 | Linden | 250/281 |

*Primary Examiner*—Bruce C. Anderson
*Attorney, Agent, or Firm*—Chilton, Alix & Van Kirk

[57] ABSTRACT

A method and apparatus for determining the elemental composition of a sample (1) by plasma mass spectroscopy comprises introducing a said sample (1) into an inductively-coupled or microwave-induced plasma formed in an inert gas to generate atomic ions from the elements present in it; passing at least some of said atomic ions through a nozzle-skimmer interface (15–21) into an evacuated chamber (23), said interface comprising electrode means (19, 39) for determining the electrical potential at which said atomic ions enter said evacuated chamber (23) so that atomic ions of a given mass-to-charge ratio enter said chamber with a particular kinetic energy; energy filtering (40) the ions entering said chamber to prevent at least molecular ions of approximately said given mass-to-charge ratio having kinetic energies less than said particular kinetic energy from passing through; and mass filtering (22) the ions passed by the energy filter and detecting those of said ions having said given mass-to-charge ratio.

20 Claims, 3 Drawing Sheets

REDUCING INTERFERENCES, IN PLASMA SOURCE MASS SPECTROMETERS

This invention relates to mass spectrometers. It is particularly useful in mass spectrometers employing a plasma ion source such as an inductively-coupled plasma (ICP) or a microwave-induced plasma (MIP) source. Such instruments typically use a quadrupole mass filter but magnetic-sector mass filters are also used. The invention is applicable to both types.

ICP and MIP mass spectrometers are characterized by low background noise and high sensitivity and may have detection limits in the parts-per-trillion region across the mass range. However, with present instruments, a limiting factor on the detection limit at certain masses (or strictly mass-to-charge ratios) is the presence of an unwanted background signal at the mass to be monitored. Such spectral interferences (usually known as isobaric interferences) may be due to isotopes of two or more different elements having approximately the same mass, to charged molecular species for example $ArO^+$, $Ar_2^+$ or oxide ions, or to doubly-charged species appearing at the same mass-to-charge ratio as a singly-charged ion.

Researchers in ICP mass spectroscopy have devoted considerable effort to establishing the mechanism of formation of these interfering molecular species in the hope that their formation can be reduced. For example, Vanhaecke, Vandecasteele, et al, in Mikrochim. Acta. 1992, vol. 108 pp 41–51 investigated the effect of various instrumental parameters (such as lens voltages, nebulizer and torch flow rates, etc) but were unable to form any general conclusions as to how isobaric interferences could be reduced. Similar work has been reported by Wang, Shen and Sheppard et al (J. Anal. Atomic Spectrom. 1990 vol 5 pp 445–449). Rowan and Houk (Appld. Spectrosc. 1989 vol 43 (6) pp 976-) teach the use of an instrument comprising two quadrupole mass analyzers in series. In this instrument the first quadrupole is not used as a mass analyzer but rather as an "RF only" quadrupole in which the pressure is deliberately kept quite high, at least in the region where the ions enter it. Molecular ions entering the first quadrupole are confined by the RF field and undergo collisions with the gas molecules therein and are lost by scattering. Atomic ions, having much smaller collisional cross-sections will however undergo fewer collisions and be transmitted to the mass analyzer. This arrangement was found to reduce some of the molecular ion interferences.

In order to further understand the processes by which different types of ions are formed in the plasma, several workers have attempted to measure the energy distribution of ions entering the mass analyzer. Peter and Höffer (J. Vac. Sci. Technol. 1987, vol A5 (4) pp 2285) report experiments carried out to determine the energy of various ions formed in an ICP using an energy filter combined with a quadrupole mass analyzer. However, the authors did not measure the energy distributions of molecular ions formed in the plasma, and merely report the results obtained without further comment as to how the information reported may be usefully employed.

A more detailed investigation of energy distributions was reported by Chambers and Hieftje (Spectrochim. Acta, 1991 vol 46B (6/7) pp 761–784). The authors used a quadrupole mass analyzer combined with a three-grid retarding potential energy filter and report the energy distributions of a variety of ions generated in an ICP. Theories are proposed concerning ion transport processes but no measurements are described on molecular ions and no conclusions are drawn concerning distinguishing between interfering ion species in an ICPMS instrument.

It is the object of the invention to provide a method for the elemental analysis of a sample by ICP or MIP mass spectrometry in which isobaric interferences from molecular and multiply charged ions are reduced. It is a further objective to provide apparatus for carrying out such a method.

In accordance with these objectives the invention provides a method of determining the elemental composition of a sample by plasma mass spectroscopy comprising the steps of:

a) introducing a said sample into an inductively-coupled or microwave-induced plasma formed in an inert gas to generate atomic ions from the elements present in it;

b) passing at least some of said atomic ions through a nozzle-skimmer interface into an evacuated chamber, said interface comprising electrode means for determining the electrical potential at which said atomic ions enter said evacuated chamber so that atomic ions of a given mass-to-charge ratio enter said chamber with a particular kinetic energy; characterized by c) energy filtering the ions entering said chamber to reduce isobaric interferences from molecular and multiple charged ions by setting the lower cut-off energy to said particular kinetic energy of said atomic ions of a given mass-to-charge ratio so as to prevent at least the molecular ions of approximately said given mass-to-charge ratio having kinetic energies less than said particular kinetic energy from passing to step d); and d) mass filtering the ions passed by step c) and detecting those of said ions having said given mass-to-charge ratio.

Conveniently, step d) may be carried out using a quadrupole mass analyzer but a magnetic sector analyzer may also be used. The energy filtration step c) may be carried out with an energy filter having sufficient resolution to distinguish the wanted atomic ions from the unwanted ions. The requirements are further discussed below. Retarding grid or plate analyzers, parallel-plate or electrostatic cylindrical or spherical analyzers or cylindrical mirror analyzers may all be employed. Preferably there should be no line-of-sight path between the point of entry of the atomic ions into the evacuated chamber and the mass analyzer used in step d).

The inventor observed that in ICP mass spectrometers certain species produced in the ICP have markedly different ion energies from other species. In particular it was noted that whereas singly charged (i.e. atomic) "analyte" species such as Be, In and U were characterised by an ion energy distribution which steadily increased with mass (eg, from about 8 eV to 12 eV, depending on the conditions of the experiment), molecular species such as $Ar_2$ and ArO, and other oxide ions, showed substantially different ion energies, in most cases lower than those of the atomic ions of similar mass-to-charge ratio.

Multiply-charged species also were found to exhibit different ion energy characteristics from typical atomic ions. It was found by experiment that by placing an energy filter between the nozzle-skimmer interface and the mass analyzer of a prior ICP mass spectrometer it was possible to prevent ions having kinetic energies lower than the kinetic energy of the atomic ions (at any particular mass-to-charge ratio) from reaching the mass analyzer, so that the interferences due to the molecular ions in particular could be substantially reduced.

The reason for the variation of ion-energy with mass-to-charge ratio, and the difference in ion-energy for molecular and atomic species of similar mass-to-charge ratios, is not fully understood. However, the former effect is consistent with the theory that ions travelling through the interface acquire approximately the same velocity by virtue of gas dynamic effects in the interface while the latter effect suggests that the molecular ions are formed in cooler portions of the plasma, or portions where the electrical potential of the plasma is lower than the atomic ions.

Any energy filter suitable for use with the invention must have sufficient resolution to distinguish between the energies of the atomic ions and the unwanted molecular ions, which is typically 1 eV or less. Many suitable types of filters are known and have been described in combination with both quadrupole and magnetic sector analyzers. In the experiments carried out by the inventor a retarding grid analyzer was used. A fine metal mesh was placed in the line of the ion beam close to the entrance aperture of the quadrupole mass analyzer. A variable voltage was applied to this mesh which selectively allowed the transmission of ions through the mesh depending on the energy of the ions. In this way it was possible to prevent ions of low energy (relative to the atomic ions of similar mass-to-charge ratio), such as molecular ions, from entering the quadrupole mass filter by setting the potential of the mesh slightly higher than the ion energy of these species.

In this configuration, analyte ions typically of higher energy were able to pass through the mesh and into the mass analyzer. In this way isobaric interferences from molecular species at the mass of the analyte ion were substantially reduced. However, a retarding grid filter comprising more electrodes would give a sharper cut off and would improve the discrimination further.

A straightforward "parallel-plate" energy filter, which deflects the trajectory of ions passing between them to an extent dependent on the ion energy, may also be employed. Preferably, however, an energy filter with focusing properties such as part-spherical or part-cylindrical analyzers, or a cylindrical mirror analyzer, can be employed. Such analyzers generally have improved energy resolution as a result of their focusing action. If a focusing analyzer is used it may advantageously replace some or all of the ion lenses provided in conventional MIP or ICP spectrometers by providing an equivalent focusing action to efficiently transmit atomic ions from the interface to the mass analyzer.

It has been explained above that the inventor found that the ion energy of the wanted atomic ions increased steadily with mass. Thus if the mass spectrometer is operated in such a way as to detect only ions having a single or a small range of mass-to-charge ratios, the kinetic energy (below which the filter will not transmit ions) may be set at a particular energy selected so that the atomic ions at that mass-to-charge ratio are transmitted but lower energy ions are rejected. However, if the spectrometer is set to scan over a wider range of mass-to-charge ratios, the kinetic energy should preferably be varied in synchrony with the scanning of the mass analyzer, i.e. at each instant the cut-off energy of the filter should be related to the energy of the ions of the mass-to-charge ratio being detected that any instant during the scan. The particular energy at each mass can be determined by an initial experiment and the calibration results so obtained can then be used by any suitable electronic control means to provide suitable electrical potentials for the electrodes of the energy filter according to the mass which the mass filter is set to transmit to the detector at any given instant.

In another embodiment a magnetic sector may be used in place of a quadrupole analyzer. PCT publication number WO89/12313 explains how such a mass analyzer may be interfaced to a plasma ion source. Typically, the electrode means comprised in the nozzle-skimmer interface is maintained at a high potential so that the ion kinetic energies are much greater than they are for the quadrupole case, as required for the magnetic sector analyzer. However, the principles of the invention are still applicable. A double-focusing sector analyzer incorporates an energy filter which in principle may be used in the way described above, but it will be noted that because of the dependence of the ion-energy on mass, for optimal operation the conventional fixed linkage between the energy filter pass energy and the accelerating potential of the analyzer should be replaced by one which takes account of that dependence.

Preferred embodiments of the invention will now be described in greater detail by way of example only and with reference to the figures in which.

Figure 1:
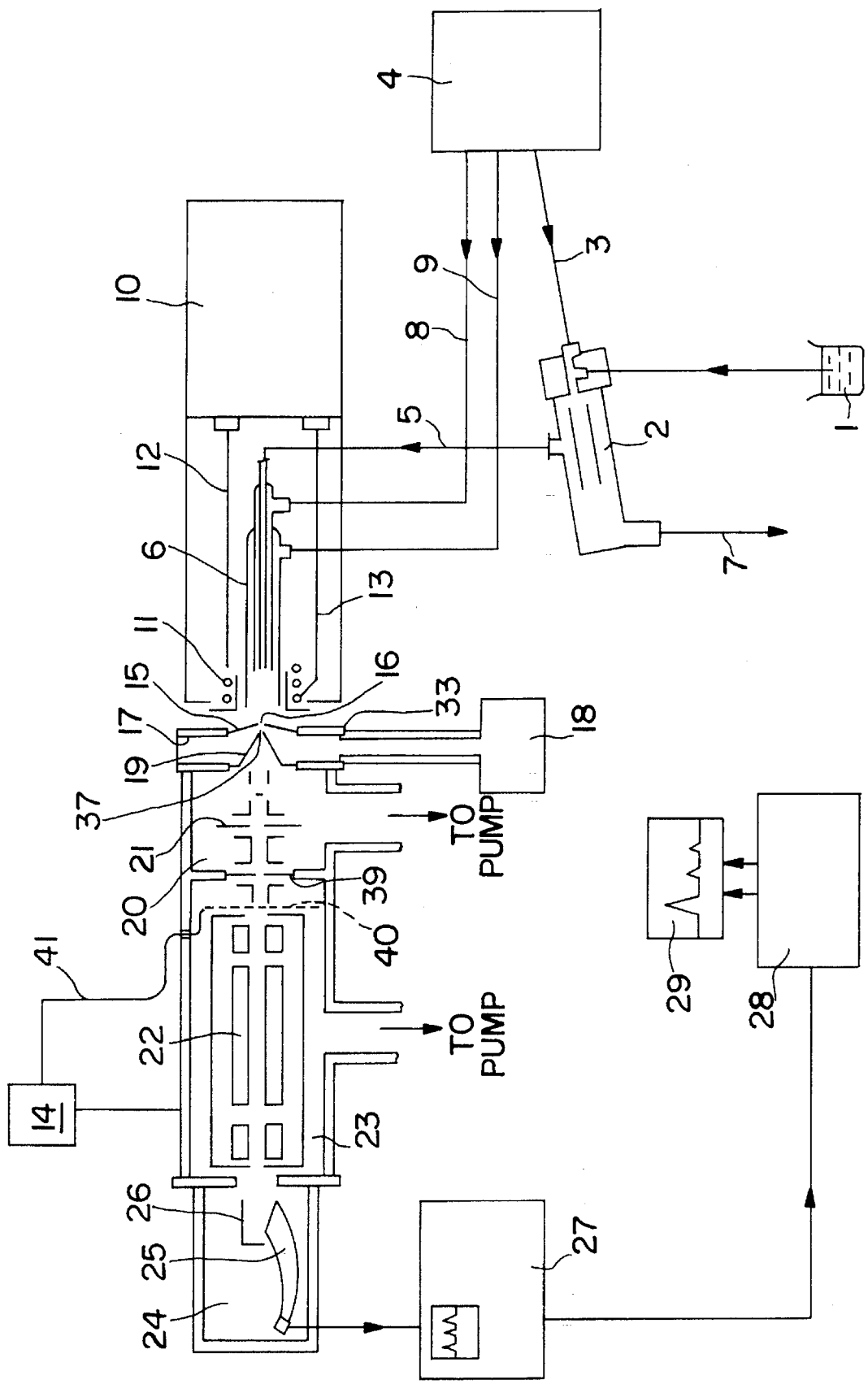
FIG. 1 is a schematic diagram of an ICP mass spectrometer incorporating a retarding grid energy filter.

Referring first to FIG. 1, means for introducing a sample into an ICP comprise a source of solution 1 of the sample which is admitted to a pneumatic nebulizer 2, supplied with a flow of argon gas from a gas supply unit 4 via a pipe 3. The sample, entrained in argon gas, is introduced into a conventional ICP torch 6 through pipe 5. Excess solution is drained from the nebulizer 2 through a drain 7. The gas supply unit 4 provides two other controlled flows of argon to the torch 6 in pipes 8 and 9.

Means for generating an inductively-coupled plasma in the inert gas substantially at atmospheric pressure comprise the ICP torch 6, mentioned above, and coil 11 which is fed with radio-frequency electrical energy via leads 12 and 13 from a generator 10. In this way an ICP is formed at the end of torch 6.

The ICP torch 6 and its associated equipment including the gas supply unit 4, coil 11, generator 10 and the nebulizer 2 are conventional items of equipment and need not be described further. Although FIG. 1 illustrates the use of a pneumatic nebulizer for introducing the sample into the plasma it is within the scope of the invention to use other methods, for example electrothermal vaporization or laser ablation.

Disposed adjacent to the ICP formed at the end of the torch 6 is a nozzle-skimmer interface comprising a sampling member 15 mounted on a cooled flange 33 and a skimmer in the form of a hollow tapered member 19. The sampling member 15 contains a first orifice 16 which communicates with a region 17 which is maintained substantially below atmospheric pressure (typically 0.01 –10 torr) by a vacuum pump 18. The hollow tapered member 19 comprises a second orifice in its narrowest end and separates the region 17 from another region 20 which is evacuated by a diffusion pump (not shown). An evacuated chamber 23, pumped by another diffusion pump (not shown) is separated from region 20 by a diaphragm 39 containing another small orifice through which may enter ions leaving the nozzle-skimmer interface through the orifice in the hollow tapered member 19. (In lower performance instruments the region 20 and its associated pump, and the diaphragm 39 may be omitted so that ions enter the evacuated chamber 23 directly through the orifice in the hollow tapered member 19).

In this embodiment the potential at which the atomic ions formed in the ICP enter the evacuated chamber is determined in part by the electrical applied to the diaphragm 39 (or the member 19 if the diaphragm 39 is omitted), which components therefore serve as electrode means for determining the potential comprised in the interface. In the case of a quadrupole mass analyzer, as shown in FIG. 1, they are typically grounded, but this is not always the case. As explained, the potential at which the ions enter the evacuated chamber, together with the plasma potential and other plasma conditions such as temperature and gas flow rates, determines the kinetic energy at which the atomic ions pass into the evacuated chamber. Although this energy is not predictable from the potentials and the plasma conditions it can be measured experimentally for ions of any given mass-to-charge ratio and providing the plasma conditions are not changed, will remain substantially constant. Thus, atomic ions of any given mass-to-charge ratio will enter the evacuated chamber 23 at a particular kinetic energy, which as the inventor has observed, is generally higher than the energy at which molecular ions enter the chamber.

Energy filtration means comprising a mesh grid electrode 40 connected by a lead 41 to a power supply 14 are disposed as shown in FIG. 1 to receive ions entering the evacuated chamber 23. Efficient ion transmission from the hollow tapered member 19 to the energy filtration means is ensured by a series of electrostatic lenses schematically illustrated at 21. The potential applied to the grid electrode 40 by the supply 14 is adjusted to prevent ions having lower energies than a given kinetic energy passing through the grid electrode. As explained, this kinetic energy is selected to be equal to the particular kinetic energy for ions of any given mass-to-charge ratio.

Ion mass filtering and detection means are provided by a quadrupole mass filter 22, disposed in the evacuated chamber 23, and an ion detector 24 comprising a converter electrode 26 and an electron multiplier 25. signal from the multiplier 25 is amplified by an amplifier in a display unit 27 which in turn feeds a digital computer 28 and a terminal 29 to allow further processing of the data. The computer also controls the function of the quadrupole analyzer 22 and the potential applied to the mesh electrode 40 by the power supply 14.

The quadrupole analyzer 22, detector 24 and the data acquisition and control system comprising items 27, 28 and 29 are conventional. Further, as explained, a magnetic sector analyzer may be substituted for the quadrupole analyzer 22. PCT publication number WO89/12313 describes a suitable interface for such an analyzer.

The method by which the apparatus illustrated in FIG. 1 is employed in the invention has been described above. In order to monitor atomic ions of a single mass-to-charge ratio the computer 28 is used to set the quadrupole analyzer 22 to transmit only ions of the desired mass-to-charge ratio to the detector 24 and to set the potential on the electrode 40 to the highest value at which those ions are transmitted. Any molecular ions of the same mass-to-charge ratio, typically of lower energy, will then be prevented from entering the mass analyzer.

In order to record part of (or the whole) mass spectrum of the atomic ions comprised in a sample, or to monitor several mass-to-charge ratios in a repetitive sequence, the computer 28 is arranged to set the mass analyzer 22 to the desired scan pattern and simultaneously adjust the potential on the electrode 40 according to the previous paragraph in sympathy with the changing mass-to-charge ratio set on the mass analyzer. The necessary potentials may be previously determined by calibration at particular mass-to-charge ratios, interpolating or extrapolating at mass-to-charge ratios where no data has been obtained.

However, it will be appreciated that if only a small range of mass is scanned (for example, a group of isotopes of a particular element) it may be sufficient to keep the potential on the electrode 40 at a constant value.

Figure 2:
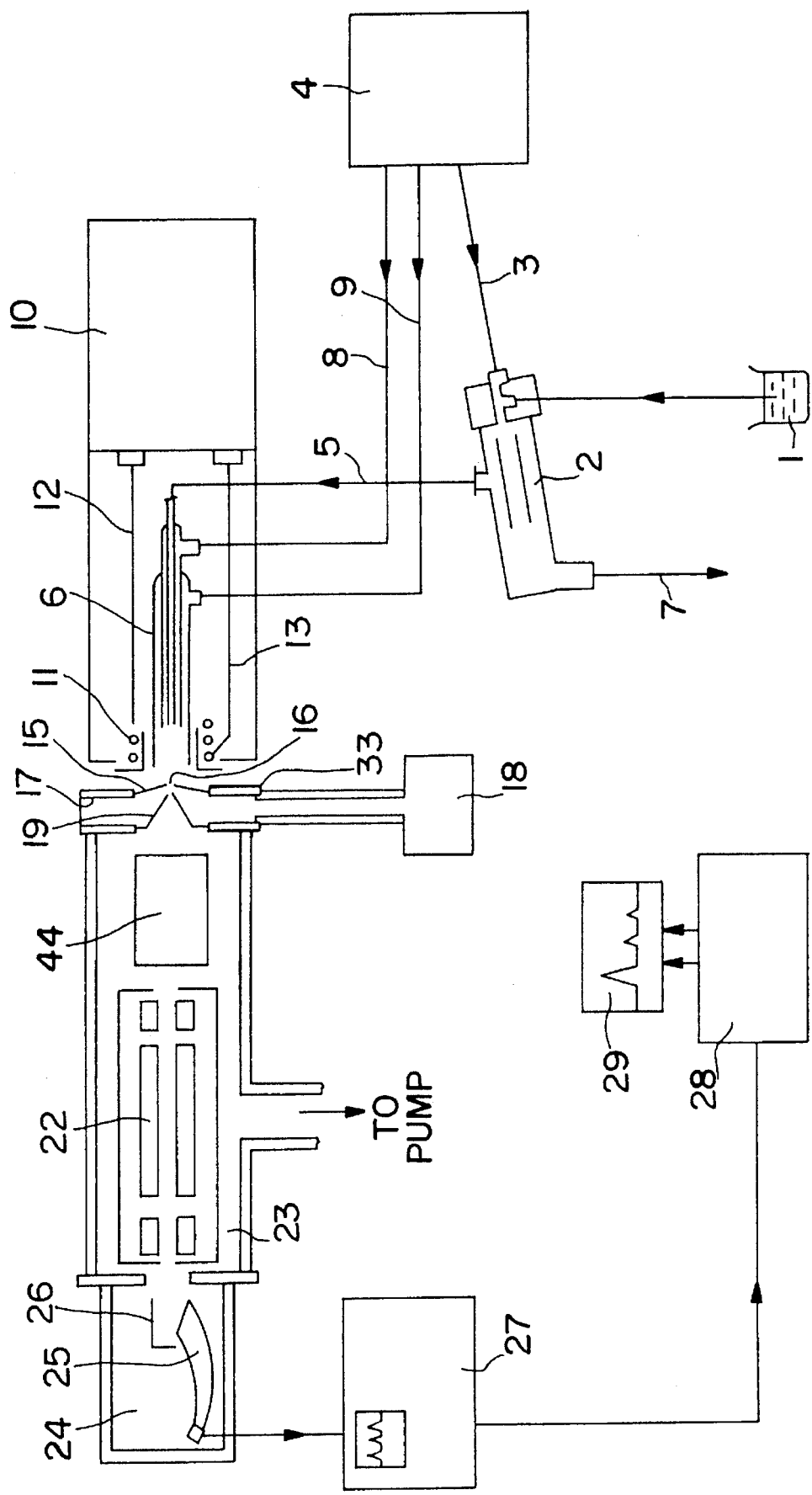
FIG. 2 is a schematic diagram of an ICP mass spectrometer comprising a cylindrical mirror analyzer.

Referring next to FIG. 2, another preferred embodiment of apparatus according to the invention comprises the major components of the FIG. 1 embodiment (identified by the same reference numerals) with the exception of the chamber 20 and diaphragm 39, the electrostatic lens system 21, and the electrode 40. In their place energy filtration means comprising a cylindrical mirror analyzer (CMA) 44 (discussed in detail below) is provided. The CMA 44 is arranged to focus the ions passing through the orifice in the hollow tapered member 19 on to the entrance aperture of the mass analyzer 22, providing those ions have the particular kinetic energy. It further prevents the passage of ions having lower energy on account of its energy filtration properties. The CMA has a definable energy window and the width and the absolute mean position of the window can be synchronised with the scanning of the mass analyzer.

Figure 3:
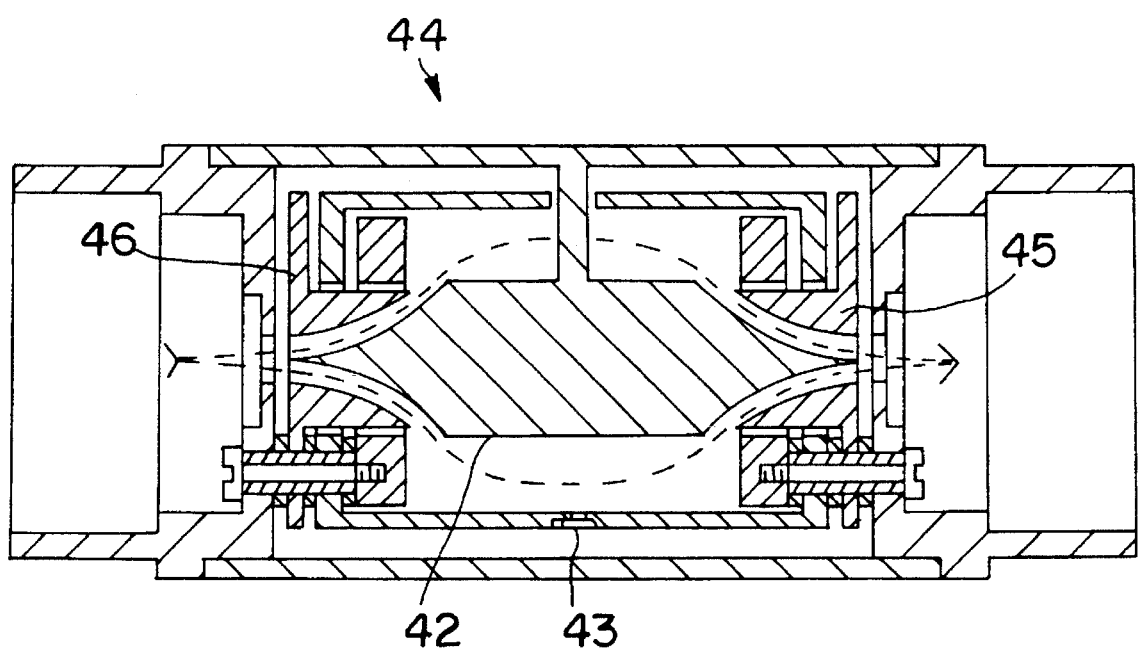
FIG. 3 is a schematic diagram of a cylindrical mirror analyzer suitable for use in the apparatus shown in FIG. 2.

FIG. 3 illustrates in more detail a CMA suitable for use in the apparatus of FIG. 2. The CMA is a cylindrical on-axis device exhibiting no direct line of sight through the device (thereby preventing the passage of photons and neutral species). It comprises an inner cylindrical solid electrode 42 and an outer cylindrical electrode 43. The method of operation of the CMA is well known and need not be discussed here. It should be pointed out, however, that the efficient combination of a CMA with a quadrupole analyzer is not straightforward because the CMA receives and focuses ions at an angle of about 42° to its axis whereas the quadrupole requires that the ions entering it have trajectories substantially aligned with the axis. In the CMA shown in FIG. 3 the interfacing is achieved by means of the shaped ends of the inner electrode 42 and the curved auxiliary electrodes 45, 46. The mode of operation of such a CMA and its combination with a quadrupole mass analyzer are fully disclosed in EP-A-0223520.

It will be appreciated, however, that other types of energy filters, such as electrostatic part-spherical or cylindrical analyzers, may also be used in the invention, and that such combinations may provide better resolution than the simple systems described above, resulting in improved discrimination between atomic and molecular ions, particularly at low mass-to-charge ratios.

I claim:

1. A method of determining the elemental composition of a sample by plasma mass spectroscopy comprising the steps of:

a) introducing a said sample (1) into an inductively-coupled or microwave-induced plasma formed in an inert gas to generate atomic ions from the elements present in it;

b) passing at least some of said atomic ions through a nozzle-skimmer interface (15, 19) into an evacuated chamber (23), said interface comprising electrode means (40) for determining the electrical potential at which said atomic ions enter said evacuated chamber (23) so that atomic ions of a given mass-to-charge ratio enter said chamber with a particular kinetic energy; characterised by c) energy filtering the ions entering said chamber (23) to reduce isobaric interferences from molecular and multiple charged ions by setting the lower cut-off energy to said particular kinetic energy of said atomic ions of a given mass-to-charge ratio so as to prevent at least the molecular ions of approximately said given mass-tocharge ratio having kinetic energies less than said particular kinetic energy from passing to step d); and d) mass filtering the ions passed by step c) and detecting those of said ions having said given mass-to-charge ratio.

2. A method as claimed in claim 1 wherein said particular kinetic energy varies with the mass-to-charge ratio and the cut-off energy in step c) is varied to correspond to the energy of the atomic ions of interest.

3. A method as claimed in claim 2 wherein said mass filtering step d) is arranged to permit the continuous detection of ions of said given mass-to-charge ratio.

4. A method as claimed in claim 3 wherein said mass filtering is carried out using a quadrupole mass analyzer.

5. A method as claimed in claim 2 wherein said mass filtering step d) is arranged to permit the sequential detection of ions having a range of mass-to-charge ratios and said energy filtering step is arranged to prevent the passage to step d) of molecular ions of approximately each of said mass-to-charge ratios having energies lower than said particular energy at each of said mass-to-charge ratios.

6. A method as claimed in claim 5 wherein said mass filtering is carried out using a quadrupole mass analyzer.

7. A method as claimed in claim 5 wherein said mass filtering is carried out using a magnetic sector analyzer.

8. A method as claimed in claim 7 wherein said energy filtering is carried out using a retarding grid.

9. A method as claimed in claim 7 wherein said energy filtering is carried out using a cylindrical mirror analyzer.

10. A method as claimed in claim 3 wherein said mass filtering is carried out using a magnetic sector analyzer.

11. A method as claimed in claim 10 wherein said energy filtering is carried out using a retarding grid.

12. A method as claimed in claim 10 wherein said energy filtering is carried out using a cylindrical mirror analyzer.

13. A method as claimed in claim 2 wherein said energy filtering is carried out using an arrangement of electrically charged parallel plates.

14. A method as claimed in claim 1 wherein said mass filtering step d) is arranged to permit the continuous detection of ions of said given mass-to-charge ratio.

15. A method as claimed in claim 1 wherein said mass filtering step d) is arranged to permit the sequential detection of ions having a range of mass-to-charge ratios and said energy filtering step is arranged to prevent the passage to step d) of molecular ions of approximately each of said mass-to-charge ratios having energies lower than said particular energy at each of said mass-to-charge ratios.

16. A method as claimed in claim 1 wherein said mass filtering is carried out using a quadrupole mass analyzer.

17. A method as claimed in claim 1 wherein said mass filtering is carried out using a magnetic sector analyzer.

18. A method as claimed in claim 1 wherein said energy filtering is carried out using a retarding grid.

19. A method as claimed in claim 1 wherein said energy filtering is carried out using a cylindrical mirror analyzer.

20. A method as claimed in claim 1 wherein said energy filtering is carried out using an arrangement of electrically charged parallel plates.

* * * * *